US008828044B2

(12) United States Patent
Aggerholm et al.

(10) Patent No.: US 8,828,044 B2
(45) Date of Patent: Sep. 9, 2014

(54) OBSTRUCTION CAPTURE AND REMOVAL DEVICE

(75) Inventors: Steen Aggerholm, St. Heddinge (DK); Bente Weber Christensen, Ringsted (DK); Per Hendriksen, Herlufmagle (DK); Thomas Lysgaard, Solroed Strand (DK); Arne Mølgaard Nielsen, Copenhagen (DK); Frank Svendsen, Ringsted (DK)

(73) Assignee: Cook Medical Technologies LLC, Bloomington, IN (US)

( * ) Notice: Subject to any disclaimer, the term of this patent is extended or adjusted under 35 U.S.C. 154(b) by 239 days.

(21) Appl. No.: 13/370,912

(22) Filed: Feb. 10, 2012

(65) Prior Publication Data

US 2012/0209312 A1   Aug. 16, 2012

(30) Foreign Application Priority Data

Feb. 11, 2011   (GB) .................................. 1102458.5

(51) Int. Cl.
*A61B 17/22* (2006.01)
*A61B 17/221* (2006.01)
*A61B 17/00* (2006.01)

(52) U.S. Cl.
CPC ....... *A61B 17/221* (2013.01); *A61B 2017/2212* (2013.01); *A61B 2017/00287* (2013.01)
USPC .......................................... 606/200; 606/127

(58) Field of Classification Search
USPC .......... 606/113, 114, 127, 200, 110–112, 128
See application file for complete search history.

(56) References Cited

U.S. PATENT DOCUMENTS

| 2,707,958 | A | * | 5/1955 | Davis ............................. 604/104 |
| 5,192,286 | A | * | 3/1993 | Phan et al. ..................... 606/127 |
| 5,368,597 | A | | 11/1994 | Pagedas |
| 6,517,550 | B1 | * | 2/2003 | Konya et al. .................. 606/113 |
| 7,052,500 | B2 | | 5/2006 | Bashiri et al. |
| 2004/0255739 | A1 | | 12/2004 | Clifford et al. |
| 2006/0224179 | A1 | | 10/2006 | Kucharczyk |
| 2008/0275464 | A1 | | 11/2008 | Abrams et al. |

FOREIGN PATENT DOCUMENTS

| AT | 195566 B | 2/1958 |
| DE | 688834 | 3/1940 |
| DE | 2436352 A1 | 2/1976 |
| DE | 3913936 A1 | 10/1990 |
| JP | 09019438 | 1/1997 |
| WO | 93/02732 A1 | 2/1993 |

OTHER PUBLICATIONS 12154535.4-1659/2486875 European Search Report Sep. 25, 2013.

* cited by examiner

*Primary Examiner* — Kathleen Holwerda
(74) *Attorney, Agent, or Firm* — Richard J. Godlewski

(57) ABSTRACT

A thrombus retrieval device (10) includes a flexible catheter (12), a retrieval wire (26) fixed to the distal end (14) of the catheter (12) and which extends out of the catheter (12) at first and second apertures in the wall of the catheter (12). A trap element (28) typically made of a porous fabric material, is attached to the catheter (12) from the distal end (14) across the location of the apertures. The trigger wire (26) can be pulled in a proximal direction, which causes the catheter (12) to twist so as to form a loop. The trap element (28), attached to the catheter at location in which it loops, forms a net for trapping thrombi or other obstructions within a patient's lumen.

18 Claims, 5 Drawing Sheets

OBSTRUCTION CAPTURE AND REMOVAL DEVICE

TECHNICAL FIELD

The present invention relates to an obstruction capture and removal device, in the preferred embodiment for the removal of thrombi or debris from blood vessels.

BACKGROUND OF THE INVENTION

Mechanical thrombectomy is a procedure which has been in widespread use for many years. Typical thrombectomy devices are balloons which are inflated in a vessel and then withdrawn to pull thrombi into a sheath and then withdrawn from the patient. Other devices are simple open ended catheters into which a thrombus is aspirated and removed from the patient. Another thrombectomy device employs a basket that is opened within the thrombus so that the thrombus becomes captured in the basket. The basket can then be retrieved taking the thrombus with it. Still other devices use a small corkscrew shaped device which is collapsed inside a catheter. The catheter is passed through the thrombus, the corkscrew is pushed out of the catheter allowing the device to expand, thereby capturing the thrombus for removal. Some corkscrew devices are simply "screwed" into the thrombus, then retracted into a catheter for removal before the corkscrew is retracted.

Known devices are disclosed in U.S. Pat. No. 7,052,500, US-2006/0,224,179 and US-2008/0,275,464.

Aspirating the thrombus into a catheter can cause breaking up of the thrombus during the procedure. Furthermore, where a thrombus is located in a very narrow vessel, the size of the catheter is too small and unable to house the thrombus within its lumen.

SUMMARY OF THE INVENTION

The present invention seeks to provide an improved obstruction removal device.

According to an aspect of the present invention there is provided an object capture device for capturing an object from a body vessel, including a flexible catheter provided with a distal end and a proximal end; at least one opening in a side of the flexible catheter, the at least one opening providing spaced catheter entry and exit points; a trigger wire located within the flexible catheter and attached to or proximate the distal end of the catheter; a flexible trap element attached to the catheter across the at least one opening; wherein retraction of the trigger wire causes the catheter element to twist into a loop about the at least one opening, said twisting action causing the trap to form a capture chamber.

In practice, the trap element is sized and arranged so as to locate relatively closely against the catheter so as to enable the device to have a small diameter, or footprint, when the catheter is in an extended, that is straight or not twisted configuration. This can be by means of a combination of the size of the trap element and the spacing of points at which it is fitted to the catheter.

The preferred embodiments of device taught herein provide a number of advantages over known art. For example, the devices taught herein are able to capture the entirety of a thrombus or debris without breaking this up during the capture or removal operation, as occurs with some prior art systems. The devices are also able to provide a complete trap able to close off the entire diameter of the vessel and thus to capture all of the thrombus or other debris material, including small fragments. The preferred devices are also able to be constructed in an introducer assembly which is flexible and has a small footprint, able to be passed through small diameter vessels and tortuous vasculature.

It is preferred that the trap element is shaped so as to create a generally conical capture chamber, thereby to have a wide opening and a narrow base.

The trap element may be made of a substantially impermeable material, possibly with one or more small openings therein, but it is preferably made from a porous material having pores sufficiently small to trap obstructing material, such as a thrombus, but large enough to allow the passage of blood or other fluid. In this regard, the trap may be made of a netting or mesh type material. An example is fine nylon mesh, which is very flexible and can retain a stable mesh size during use.

The trap element is preferably attached to the catheter across the location of the hole or holes. Thereby, the twisted loop will form the entry point into the trap and will also provide a support at the opening.

In the preferred embodiment, the catheter is provided with at least first and second longitudinally spaced holes in its side wall. The trigger wire, which normally passes within the lumen of the catheter, passes out through one hole and then back into the catheter lumen through the second hole. The distal end of the trigger wire is fixed to or proximate the distal end of the catheter. Thus, when the trigger wire is pulled back, this will cause the catheter to twist between the first and second holes and thus to cause the trap element to conform to the chamber configuration.

There may be provided more than two holes in the catheter wall. Having a greater number of holes enables a choice of entry and exit points for the trigger wire, thus the size of twisted loop which is formed on puling back of the wire. Similarly, by providing multiple pairs of entry and exit points, a plurality of twisted loops can be created in the catheter, preferably for a plurality of trap chambers (formed either from a single trap element or from a plurality of trap elements).

In an embodiment, there may be provided in the catheter a single opening. In this embodiment, the opening would extend longitudinally along the catheter, in the form of a slot, with the ends of the opening providing the entry and exit points for the trigger wire. Upon pulling of the trigger wire, this will be pulled out of the catheter through the slot and thus be able to twist the catheter into the loop.

Advantageously, the entry and exit points provided by the opening or openings are spaced so as to form a twisted loop which has a diameter substantially equivalent to the diameter of the lumen into which the device is to be used.

The catheter may provide, through the lumen described above or through a different lumen, a lumen for a guide wire. In the case of a single lumen, the trigger wire may be positioned to a side of the wall of the catheter.

Preferably, there is provided an introducer sheath through which the device can be fed to the target site.

According to another aspect of the present invention, there is provided a method of capturing an object from a body vessel by means of a device including a flexible catheter provided with a distal end and a proximal end; at least one opening in a side of the flexible catheter, the at least one opening providing spaced catheter entry and exit points; a trigger wire located within the flexible catheter and attached to or proximate the distal end of the catheter; a flexible trap element attached to the catheter across the at least one opening; the method including the steps of: locating the device is a patient's vessel; retracting the trigger wire in a proximal direction thereby to cause the catheter element to twist into a loop about the at least one opening and the trap to form a capture chamber; and trapping an object within the capture chamber.

Preferably the method includes the step of removing the object from the patient while the object is retained in the trap.

BRIEF DESCRIPTION OF THE DRAWINGS

Embodiments of the present invention are described below, by way of example only, with reference to the accompanying drawings, in which.

DETAILED DESCRIPTION OF THE PREFERRED EMBODIMENTS

It is to be understood that the Figures are schematic and do not show the various components to their actual scale. In many instances, the Figures show scaled up components to assist the reader in the understanding of the features disclosed therein.

In this description, the term distal is used to refer to an end of a component which in use is furthest from the surgeon during the medical procedure, including within a patient. The term proximal is used to refer to an end of a component closest to the surgeon and which, in practice, may be in or adjacent an external manipulation part of the deployment or treatment apparatus.

Figure 1:
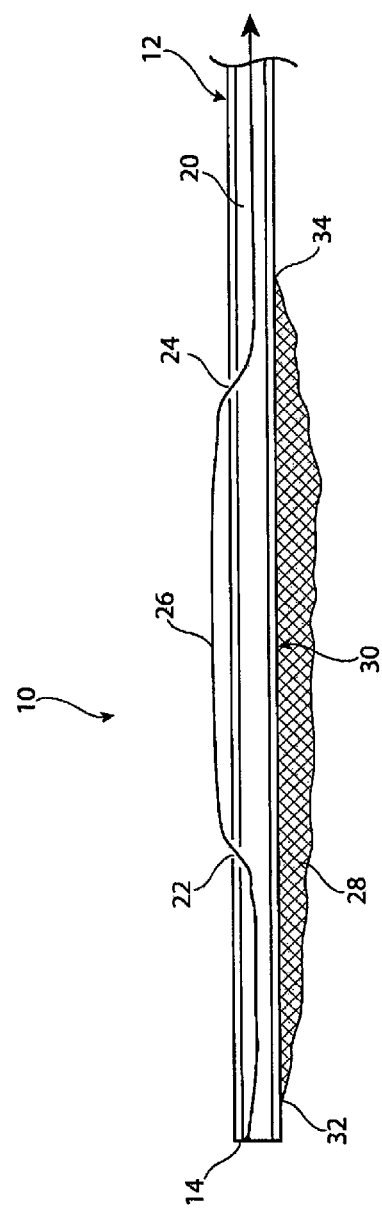
FIG. 1 shows schematically an embodiment of object removal device in an extended, delivery, configuration.

Referring now to FIG. 1, there is shown schematically an embodiment of object removal device 10 which can be used for retrieving obstructions, such as thrombi, from patient vessels. The device 10 shown in FIG. 1 would typically be introduced into the vasculature of a patient via a carrier sheath, of a type well known in the art.

The device 10 includes a flexible catheter 12 having a distal end 14. The catheter 12 also has a proximal end 36, shown schematically in FIG. 2, which extends to an external manipulation end or handle unit 38 of the device 10. The proximal end 36 of the catheter 12 would remain outside the patient during the medical procedure, which allows for control and operation by a clinician.

The catheter element 12 is preferably made of a flexible and relatively springy material, such as a plastics material or even a metal. It is envisaged also that the catheter 12 could be made of a shape memory material to provide this with the desired elasticity.

The catheter 12 has a lumen 20 extending through substantially its entire length (it could, however, be closed off at its distal end 14 in some embodiments). Proximate its distal end 14, the catheter 12 has distal and proximal apertures or holes 22, 24 in its wall.

A trigger wire 26, is in this embodiment is fixed to the distal end 14 of the catheter 12 and passes from within the lumen 20 of the catheter 12 out of the aperture 22 then back into the lumen 20 through the proximal aperture 24. The trigger wire 26 is fixed at or close to the distal end 14 of the catheter 12 by any suitable mechanism such as bonding, tying (knotting), welding and so on.

Figure 2:
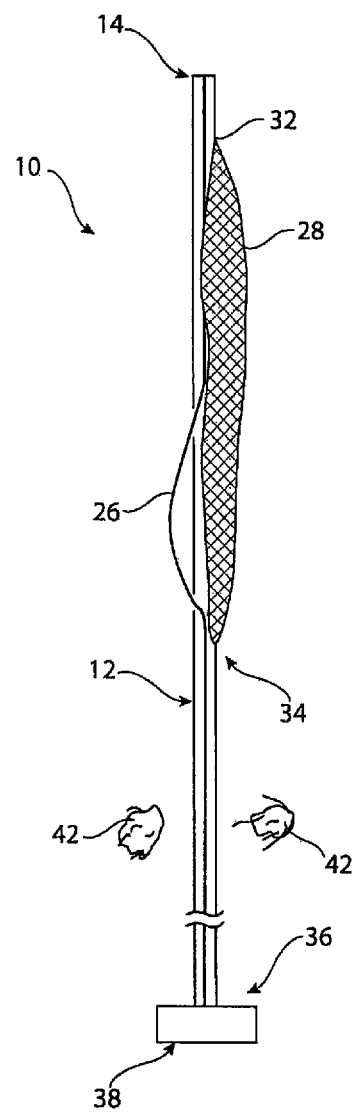
FIG. 2 shows the device of FIG. 1 in a position prior to deployment.

With reference to FIG. 2, the trigger wire 26 extends through the lumen 20 of the catheter 12 to the proximal end 36 of the device 10, that is in practice to the external manipulation unit 38. The trigger wire 26 is thus held at its distal end but loose at its proximal end.

The trigger wire 26 can be made of any of the materials commonly used in introducer assemblies, including steel, Nitinol, for example.

Attached to the catheter 12 is a flexible trap element 28, which is fixed to the outer surface of the catheter 12 along two of its edges 30. As can be seen in the drawings, the trap element 28 extends from close to the distal end 14 of the catheter, indicated as location 32, to a location 34. Typically, as will become apparent from the description which follows, the edges 30 of the trap element 28 are fixed to the catheter 12 for at least a distance (L), which is substantially equal, in the preferred embodiment, to the circumference of the trap once deployed and preferably also substantially equal the circumference of the vessel in which the device 10 is used.

The trap element 28 is advantageously made from a porous fabric material such as a mesh or netting, although it could equally be made of a non-porous material with at least one aperture therein to allow the flow of fluid therethrough. An example of material is fine nylon mesh, which is very flexible and can retain a stable mesh size during use.

It is preferred that the trap 28 is of a type which can trap all required debris and yet which allows the flow liquid therethrough including blood plasma. In practice, the material forming the trap 28 will have pore sizes sufficient to trap thrombus particles.

Referring now to FIG. 2, there is shown the proximal end of the assembly 10, which includes the proximal end 36 of the catheter 12, which is attached to an external manipulation unit 38 shown only schematically in FIG. 2 but which would have a form and components readily appreciated by the person skilled in the art.

In FIG. 2 the trigger wire 26 is shown to curve out of the catheter 12 but this is only for the purposes of explanation. In practice, the trigger wire 26 rests close to, and in some embodiments within, the catheter 12 when the assembly is in its straight configuration as shown in FIGS. 1 and 2.

The trigger wire 26 is able to be pulled in a proximal direction at the external manipulation end 38 of the device 10. This action causes the trigger wire 26 to pull the distal end 14 of the catheter 12 proximally, by virtue of the trigger wire 26 being fixed to the distal end 14. It is to be appreciated that this pulling force will act against the stiffness of the catheter 12, particularly at the location of the holes 22, 24 and thus of the trap element 28.

Figure 3:
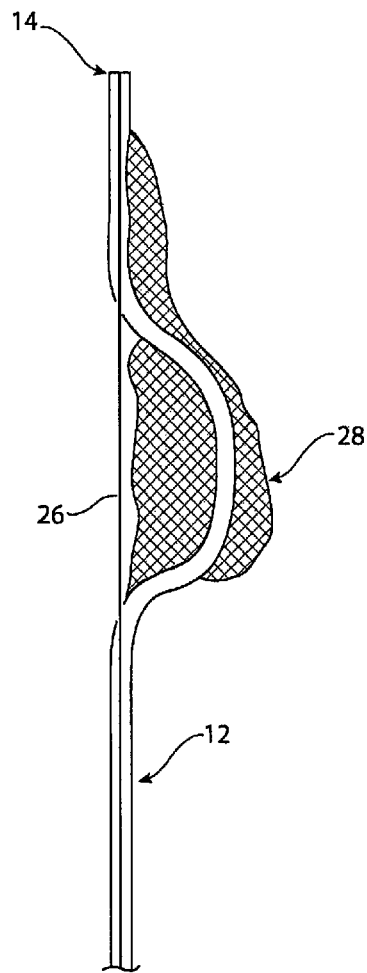
FIG. 3 shows the device of FIG. 1 at the start of the process of pulling the trigger wire thereof.

FIG. 3 shows the trigger wire 26 having been pulled sufficiently as to cause the distal end of the catheter 12 to begin to flex into a curve, in practice causing the holes 22, 24 to come closer together as the trigger wire 26 is effectively shortened.

Figure 4:
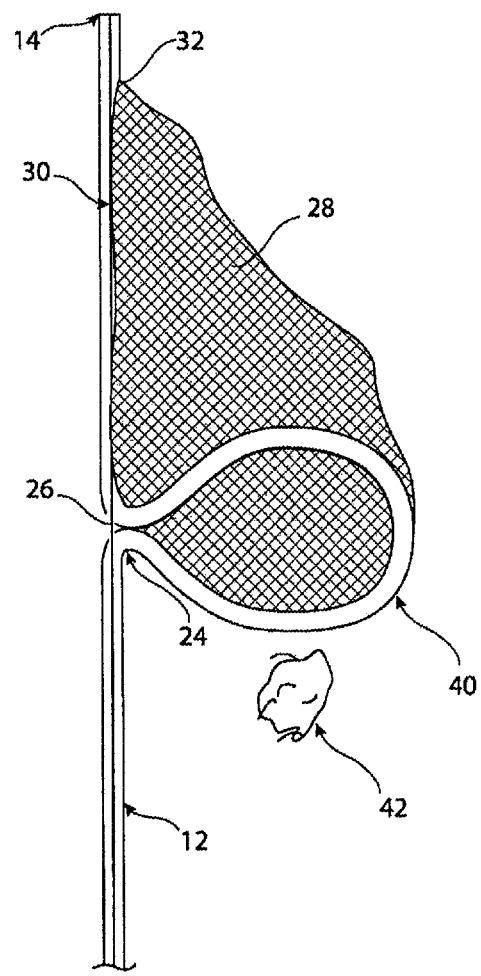
FIG. 4 shows the device of FIG. 1 with the trigger wire pulled back fully and the catheter twisted into a loop.

FIG. 4 shows the trigger wire 26 having been pulled to the maximum amount, such that the catheter at the holes 22, 24 come into abutment with one another. At this point, the catheter 12 has bent into a loop 40 and the trap element 28 has taken the form of a closed conical net. In particular, the trap element 28 opens with the loop 40, by virtue of being attached to the catheter 12, and is closed at its distal end 32 by virtue of its edges or sides 30 being likewise fixed to the catheter wall.

FIG. 4 is to be taken as a schematic illustration of the device in that the loop 40 is shown to be laterally offset from the remainder of the catheter 12. In practice this offset will not exist or would be minimised, to ensure that the loop 40 in practice can extend across the entirety of the width of a vessel.

There can be seen in FIG. 4 a thrombus 42 just proximally of the trap 28 and which in practice will be caught within the trap 28 as fluid flows through the trap.

Once the obstruction has been caught in the trap 28, the pulling force applied to the trigger wire 26 can be released. So doing causes, in light of the resiliency of the device, the catheter element 12 to regain its straightened shape as shown in FIGS. 1 and 2 or a configuration approaching this. The thrombus 42 or other obstruction captured within the trap 28 would be retained within the material of the trap 28. This allows for easy removal of the device 10 from within a patient's vasculature (typically through a carrier sheath (not shown)), with the obstruction held therewithin.

The assembly shown in FIGS. 1 to 4 could have a catheter 12 which has consistent characteristics such as flexibility throughout its length. The arrangement of the trigger wire 26 and the holes 22, 24 in this embodiment would sufficient cause the catheter to flex into the loop 40 shown in FIG. 4. In other embodiments, the catheter 12 may be more flexible around its distal end 14, typically from around the position of the proximal hole 24, compared to the remainder of its extend. This may be achieved by making the catheter 12 of different materials along its length, by thinning the walls of the catheter 12 at this location or in any other suitable manner.

Figure 5:
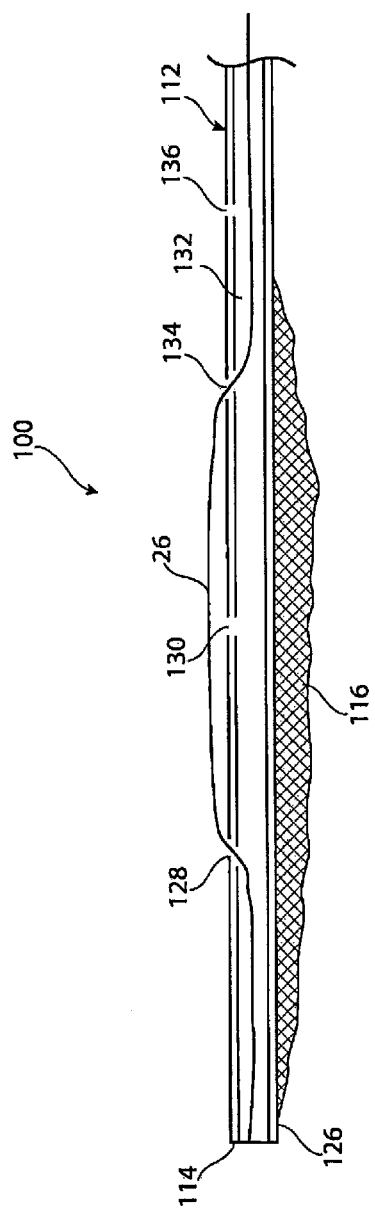
FIG. 5 shows detail of the distal end of another embodiment of the device of FIG. 1.

FIG. 5 shows a slightly different embodiment of device 100, having the same characteristics as the embodiment taught above, differing in having a plurality of apertures 128, 130, 134, 136 therein. These apertures enable the trigger wire 26 to be fed into and out of the lumen 132 in a plurality of different configurations, thereby to be able to create different sized loops of twisted catheter 112 when the trigger wire 26 is pulled back. In a preferred embodiment, there would be provided a plurality of trigger wires, each coupled through a respective aperture and marked for the clinician's reference. Pulling on one of the trigger wires will cause the trap to form, of a size related to the position of that trigger wire. Thus, the characteristics of the trap element can be varied.

It is also possible by this arrangement to form a plurality of different loops 40 within the device 100, in one embodiment by providing a plurality of different sections of trap material 116. This would be achieved, for instance by having the trigger wire 26 extend out in two different locations of the catheter element 112. This embodiment has the advantage of being able to adjust the characteristics of the trap in a single device to suit different lumen sizes.

The number of apertures that the catheter 112 could be chosen as desired and preferred, and so can the relative spacings from one aperture to another.

Figure 6:
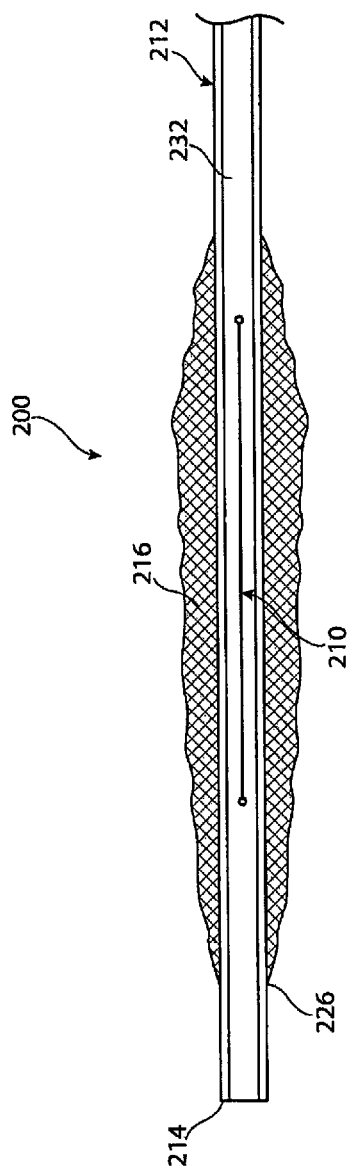
FIG. 6 shows detail of the distal end of yet another embodiment of the device of FIG. 1.

FIG. 6 shows yet another embodiment of retrieval device 200 which includes a flexible catheter 212 having a lumen 232 therein and a distal end 214. A trap element 216 is attached to the catheter 212. The catheter 200 has characteristics equivalent to those of the embodiments described above. In place of a plurality of openings in the wall of the catheter 12, the embodiment FIG. 6 has a single opening which is in the form of a slot 210. The slot 210 may have enlarged apertures at its ends, as shown in the Figure. The slot 210 allows the trigger wire (not shown in FIG. 6) to extend out of the slot 210 when this is pulled, in order to cause the catheter 212 to twist and loop in the manner shown, for example, in FIGS. 3 and 4.

It would also be possible to locate the trigger wire on the outside of the catheter 212, for instance by fixing this at points along the catheter 12, for example through fixing hooks which allow the catheter to twist and loop when the trigger wire is pulled. In such an event, it would not be necessary to have a catheter with a lumen but have simply a flexible rod or wire.

In the embodiments which use a catheter, the lumen within the catheter can be used also for a guide wire of known form. In this regard, the catheter may have a single lumen 20, 132, 232 which would accommodate both the trigger wire and a guide wire or could be a multi-lumen catheter. The catheter can also be used for other purposes, such as for flushing and the like.

It is envisaged that the device 10, 100, 200 will have a very small footprint, that is have a very small outer diameter, particularly in some embodiments, in order for this to be useable also very small lumens, such as the cerebral arteries. The device 10, could for instance, have a diameter of the order of 6 French or less. Of course, the device could also usefully be designed for treatment within larger vessels such as the main arteries.

It is not excluded that the device 10, 100, 200 could form a loop 40 which is smaller than the diameter of the lumen within which the device is deployed, in which case the clinician would steer the loop 40 within a patient's vessel in order to catch a thrombus like the obstruction to be retrieved.

The disclosure of the abstract accompanying this application is incorporated herein by reference.

What is claimed is:

1. An object capture device for capturing an object from a body vessel, including:
   a flexible catheter provided with a distal end and a proximal end;
   at least one opening in a side of the flexible catheter, the at least one opening providing spaced catheter entry and exit points for a trigger wire;
   a trigger wire located within the flexible catheter and attached to or proximate the distal end of the catheter, the trigger wire passing out of the catheter through the exit point and then back into the catheter through the entry point;
   a flexible trap element attached to the catheter across the at least one opening, the trap element being detached from the trigger wire; and
   wherein retraction of the trigger wire causes the catheter to twist into a loop about the at least one opening, said twisting action causing the trap element to form a capture chamber.

2. A device according to claim 1, wherein the at least one opening comprises a slot with two ends, the slot extending longitudinally along a portion of the catheter, the ends of the slot providing the entry and exit points for the trigger wire.

3. A device according to claim 1, wherein the trap element is sized and arranged so as to locate relatively closely against the catheter when the catheter is in a straight configuration.

4. A device according to claim 1, wherein the trap element is shaped so as to create a generally conical capture chamber.

5. A device according to claim 1, wherein the trap element is made of a porous material.

6. A device according to claim 5, wherein the trap element has holes or pores sufficiently small to trap obstructing material and large enough to allow the passage of blood.

7. A device according to claim 1, wherein the trap element is made of a substantially impermeable material provided with one or more openings therein.

8. A device according to claim 1, wherein the trap element is attached to the catheter across the location of the at least one opening.

9. A device according to claim 1, wherein the opening comprises at least first and second longitudinally spaced holes in the wall thereof.

10. A device according to claim 1, wherein a distal end of the trigger wire is fixed to or proximate the distal end of the catheter.

11. A device according to claim 1, wherein the catheter is provided with more than two holes in a wall thereof.

12. A device according to claim 1, wherein the entry and exit points provided by the opening or openings are spaced so as to form a twisted loop which has a diameter substantially equivalent to the diameter of the lumen into which the device is to be used.

13. A device according to claim 1, wherein the catheter provides a lumen for a guide wire.

14. A device according to claim 1, wherein the trap element is made of nylon mesh.

15. An object capture device for capturing an object from a body vessel, including:
  a flexible catheter provided with a distal end and a proximal end, the proximal end remaining outside of the patient during a procedure;
  at least one opening in a side of the flexible catheter, the at least one opening providing spaced catheter entry and exit points for a trigger wire;
  a trigger wire located within the flexible catheter and attached to or proximate the distal end of the catheter, the trigger wire passing out of the catheter through the exit point and then back into the catheter through the entry point;
  a flexible trap element attached to the catheter across the at least one opening, the trap element comprising at least two edges and fixed to an outer surface of the catheter along two of the edges;
  wherein retraction of the trigger wire causes the catheter to twist into a loop about the at least one opening, said twisting action causing the trap element to form a capture chamber.

16. A device according to claim 15, wherein the trap element is detached from the trigger wire.

17. An object capture device for capturing an object from a body vessel, including:
  a flexible catheter provided with a distal end and a proximal end, the proximal end remaining outside of the patient during a procedure;
  an opening in a side of the flexible catheter extending longitudinally along the catheter in the form of a slot, with the ends of the slot providing an entry point and an exit point for the trigger wire; a trigger wire located within the flexible catheter and attached to or proximate the distal end of the catheter, the trigger wire passing out of the catheter through the exit point and then back into the catheter through the entry point;
  a flexible trap element attached to the catheter across the opening, the trap element comprising at least two edges and fixed to an outer surface of the catheter along two of the edges;
  wherein retraction of the trigger wire causes the catheter to twist into a loop about the opening, said twisting action causing the trap element to form a capture chamber.

18. A device according to claim 17, wherein the trap element is detached from the trigger wire.

* * * * *